United States Patent
Rojas et al.

(10) Patent No.: US 7,182,952 B2
(45) Date of Patent: Feb. 27, 2007

(54) UREA AND NITROGEN BASED COMPOUNDS AS FEEDING STIMULANTS/AGGREGANTS AND MASKING AGENTS OF UNPALATABLE CHEMICALS FOR SUBTERRANEAN TERMITES

(75) Inventors: Guadalupe M. Rojas, Metairie, LA (US); Juan A. Morales-Ramos, Metairie, LA (US); David R. Nimocks, III, Fayetteville, NC (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/939,871

(22) Filed: Sep. 13, 2004

(65) Prior Publication Data

US 2005/0042246 A1    Feb. 24, 2005

Related U.S. Application Data

(62) Division of application No. 09/748,036, filed on Dec. 22, 2000, now Pat. No. 6,824,787.

(51) Int. Cl.
*A01N 25/08*    (2006.01)

(52) U.S. Cl. .................. 424/405; 424/84; 424/406; 424/410; 424/413; 424/DIG. 11; 514/554; 514/588

(58) Field of Classification Search ........ 424/405–421, 424/84
See application file for complete search history.

(56) References Cited

U.S. PATENT DOCUMENTS 6,203,811 B1 *   3/2001   McPherson et al. ........ 424/405

FOREIGN PATENT DOCUMENTS

JP         2000 7516       *   1/2000

OTHER PUBLICATIONS

Henderson et al Feeding Stimulants-Termites, The international Research Group on Wood Preservation- presented @ Bali, Indonesia, May 29-Jun. 3, 1994.*

* cited by examiner

*Primary Examiner*—Neil S. Levy
(74) *Attorney, Agent, or Firm*—John D. Fado; Randall E. Deck; Lesley Shaw

(57) ABSTRACT

Nitrogen containing compounds are effective as subterranean termite feeding stimulants/aggregants and as masking agents for concealing the presence of other compounds which are repellents to termites, when they are used in low concentrations, less than or equal to about 1000 ppm (0.1%, by weight). The nitrogen containing compounds may be formulated alone, or optionally in a bait or in combination with other compounds effective for controlling or marking subterranean termites.

25 Claims, 1 Drawing Sheet

UREA AND NITROGEN BASED COMPOUNDS AS FEEDING STIMULANTS/AGGREGANTS AND MASKING AGENTS OF UNPALATABLE CHEMICALS FOR SUBTERRANEAN TERMITES

BACKGROUND OF THE INVENTION

1. Field of the Invention

The invention relates to compositions effective as feeding stimulants/aggregants for subterranean termites and for masking the presence of other chemicals to subterranean termites.

2. Description of the Prior Art

Damage in the United States attributable to subterranean termites is now estimated to be in excess of one billion dollars a year. All wooden or wood-containing structures are potentially affected, including homes, outbuildings, fences, utility poles, railway sleepers, boats, bridges, retaining walls and even living trees. Of perhaps even greater concern, the Formosan subterranean termite, *Coptotermes formosanus*, has become one of the most destructive pests in the contiguous United States since its introduction to this country within the last half-century. Reasons for this include their massive colonies which can contain tens of millions of individuals, their ability to attack several species of living trees, and their high level of reproduction.

The most successful existing methods for control of subterranean termites are preventive rather than remedial. These include barrier treatments to structures and the pre-emptive treatment of wood materials with chemicals to prevent termite attack. These however have drawbacks. Physical barriers are not compatible for retrofitting on many existing constructions and may not be completely effective, and chemical treatments are only partially effective and last only about five years.

Baits have been increasingly utilized for monitoring and/or controlling subterranean termites. Typical commercially available baits include a cellulose containing material as a food source, provided within a termite accessible housing or container. These bait stations are placed beneath the soil in an area where termites are suspected, and periodically monitored for evidence of termite feeding or infestation. Upon indication of termites, the cellulose containing material may be replaced with a new bait containing a cellulose containing material in combination with a termiticide such as a slow-acting toxicant or termite growth regulator.

Using baits to deliver a termiticide has several advantages. Baits typically require only a small amount of the termiticide, and they target only the termites that feed on the bait. Thus non-target organisms are not affected. Moreover, the use of a bait often makes it unnecessary to locate the nest. Because many termites, including the Formosan termite, *C. formosanus,* distribute food to other termites in the colony, the termiticide laced food may be spread throughout a colony after feeding by only a few foraging termites. Baits utilizing low toxicity termiticides in this manner have shown success in reducing damage caused by subterranean termites. Baits containing diflubenzuron and hexaflumuron have been particularly effective in suppressing large colonies of *C. formosanus*.

However, conventional baits suffer from several disadvantages. Subterranean termites may typically find their food by random probing. Consequently, without anything to attract the termites, the bait stations are often bypassed and left uneaten. Moreover, many termiticide or other compounds incorporated into baits are repellant to the termites, limiting the use of such agents. The present state of the art is limited to the use of a few non-repellant termiticides and low concentrations, less than 100 ppm, of some effective but moderately repellant termiticides. This increases both the time and the amount of bait which must be consumed by the termites for the termite colony to attain lethal levels of the active compound. It also increases the likelihood that the termites may learn to avoid feeding on the bait before such levels are attained.

While various methodologies and compositions have been developed, there remains a need for improved methods and compositions for monitoring and controlling termites.

SUMMARY OF THE INVENTION

We have discovered that nitrogen containing compounds are effective as subterranean termite feeding stimulants/aggregants and as masking agents for concealing the presence of other compounds which are repellent to termites, when they are used in low concentrations, less than or equal to about 1000 ppm. The nitrogen containing compounds may be formulated alone, or optionally in a bait or in combination with other compounds effective for controlling or marking subterranean termites.

In accordance with this discovery, it is an object of this invention to provide compositions and methods for stimulating feeding and aggregating subterranean termites.

Another object of this invention is to provide compositions and methods for controlling termite populations.

It is also an object of this invention to provide compositions and methods for monitoring and/or marking termites.

A further object of this invention to provide a method and composition effective for masking or reducing the repellency to termites of compounds such as termite toxicants, growth regulators, and colorants.

Yet another object of this invention is to provide an improved bait composition effective as a termiticide or termite colorant delivery system at higher concentrations than previously attainable.

Other objects and advantages of this invention will become readily apparent from the ensuing description.

DETAILED DESCRIPTION OF THE INVENTION

Figure 1:
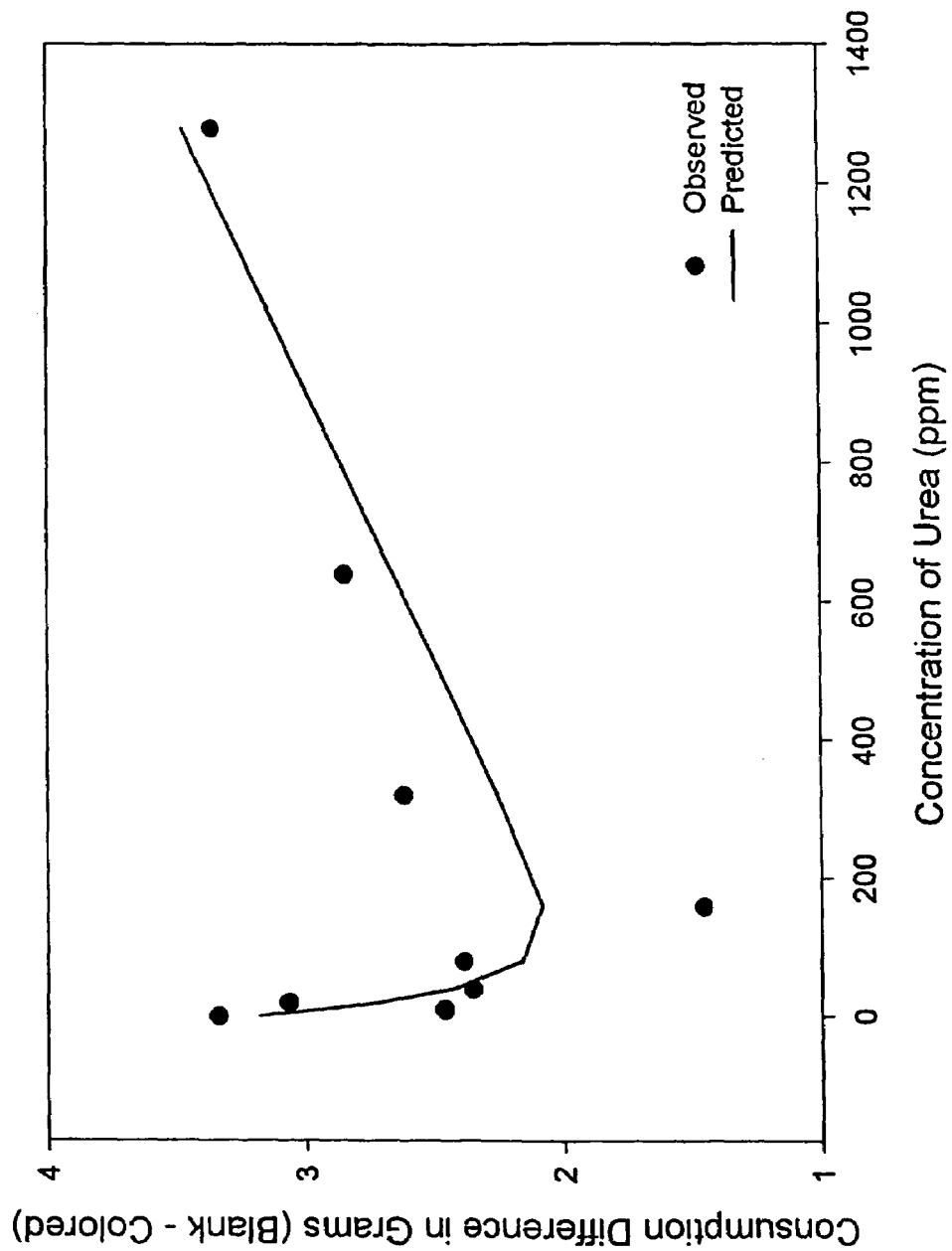
FIG. 1 shows the difference of consumption (in grams) by groups of 300 Formosan subterranean termites between a blank bait matrix vs. a bait matrix containing 1,000 ppm of the colorant neutral red, added as a feeding deterrent, and varying concentrations of urea, in a two choice experiment.

According to this invention, there is provided compositions which include low concentrations of nitrogen containing compounds that are effective as both feeding stimulants/aggregants (hereinafter referred to as aggregants) for stimulating subterranean termite feeding and aggregation, and/or for reducing the repellency of other compounds to termites. We have unexpectedly discovered that the affinity or aggregation of termites to these nitrogen containing compounds is significantly increased when they are used at concentrations less than or equal to about 1,000 ppm (i.e., 0.1%, by weight), in comparison to the use of the same compounds at higher levels, particularly greater than or equal to 2500 ppm. As described herein, in their capacity as feeding stimulants/aggregants, these low levels of the nitrogen containing compounds induce active foraging and stimulate feeding thereon by the subterranean termites. Aggregation of the termites then occurs as a consequence of this feeding stimulation, with greater numbers of termites being recruited or brought to the site to feed on the nitrogen containing compounds or baits containing the compounds.

Moreover, we have further discovered that at these low levels (i.e., less than or equal to about 1,000 ppm), the same nitrogen containing compounds are effective for masking or camouflaging the presence of a wide variety of compounds from the termites. Many chemicals such as insecticides, termite growth regulators, and colorants are normally repellent to subterranean termites, limiting the dosage at which they may be used in baits or, in some instances, precluding their use at any effective level. However, when they are used in combination with the low levels of the nitrogen containing compounds of this invention, the ability of the termites to detect these otherwise repellent chemicals may be significantly reduced. These chemicals may now be provided at higher concentrations in termite baits than previously attainable without reducing the consumption of the bait by the target termites.

Nitrogen containing compounds suitable for use as termite attractants and masking agents in accordance with this invention include ammonium salts and amine containing compounds, which amine containing compounds are exclusive of amino acids (i.e., naturally occurring amino-acids of proteins, as described by Lehninger, Biochemistry, second edition, Worth publishing, New York, pp. 71–77, 1975, the contents of which are incorporated by reference herein), polypeptides, and proteins. Preferred amine containing compounds include but are not limited to urea and its derivatives, also referred to as ureido compounds, such as benzylurea and dibenzylurea (carbanilide); uric acid, its isomers and derivatives, such as tauto-uric acid; amino benzoic acid; aminobenzoyl glutamic acid; amino butyric acid; aminonicotinic acid; aminophenol; aminosalicylic acid; aminonaphthols and aminonaphthoic acid; aminopurine (adenine); aminopyridine; benzylamines such as 6-benzylaminopurine 9-(B-D-glucoside) and 6-benzylaminopurine riboside; synthetic sweeteners such as aspartame; and glucosamine. Preferred ammonium salts include but are not limited to ammonium fluoride and the ammonium salt of molibdic acid. Use of urea and uric acid is particularly preferred. The skilled practitioner will further recognize that the nitrogen containing compounds of this invention do not encompass nitrogen containing insecticides and termite growth regulators which have been previously disclosed, and exhibit no significant toxicity to termites at the concentration levels less than or equal to about 1,000 ppm disclosed herein.

The nitrogen containing compounds encompassed herein are effective for use with subterranean termite species belonging to the families *Rhynotermitidae* and *Kalotermitidae,* and particularly *Coptotermes formosanus* and *Reticulitermes flavipes.*

While the nitrogen containing compounds of the invention may be used as an aggregant alone, they are preferably used in combination with one or more optional additives such as water, humectants, bait matrices, termiticides, and colorants. Moreover, the nitrogen containing compounds and these other additives may be formulated in a single or separate compositions.

Suitable formulations of the nitrogen containing compounds include the compounds in crude or impure form, or in substantially pure form. However, as a practical matter, it is expected that substantially pure compounds will be formulated with a bait matrix or an inert carrier for use as a termite aggregant composition. Water is a particularly preferred carrier, although other inert carriers suitable for use herein include but are not limited to alcohols, ethers, glycols, ketones, esters, and solid carriers such as clays, silicas, cellulosics, rubber, or synthetic polymers. Subterranean termites are normally attracted to and reliant upon the presence of moisture. Therefore, combination of the nitrogen containing compounds with moisture is particularly preferred to further increase the attractiveness of the composition to the termites. In this event, the water may be provided with a humectant such as methylcellulose or polyacrylamide to maintain the moisture content in the aggregant composition. Although water is generally preferred for use herein, other inert carriers are also suitable, and may even be preferred for example, when using non-water soluble termiticides, colorants, or other additives.

In one particularly preferred embodiment, the nitrogen containing compounds are incorporated into a bait matrix upon which the targeted termite will feed and which may be placed at least partially below the soil surface. Cellulose containing materials are preferred for use as bait matrices. Suitable cellulose-containing materials include, but are not limited to paper, paper products (e.g., virgin paper, recycled paper, or a combination of both), cotton linter, cardboard, paperboard, wood, sawdust, wood particles or wood flour, processed or purified cellulose, cellulose derivatives such as cellulose ethers, and including, for example, methylcellulose, hydroxypropylmethylcellulose, and hydroxybutylmethylcellulose, or other agricultural fibers. A particularly preferred bait matrix for use herein is described by Rojas et al. (U.S. patent application Ser. Nos. 09/294,499, filed Apr. 20, 1999, and 09/625,940, filed Jul. 26, 2000), the contents of which are incorporated by reference herein.

In another preferred embodiment, the nitrogen containing compounds are provided in combination with a termiticide effective for controlling the population of the targeted termite population. As used herein, the term "termiticide" refers to a material or mixture of materials which induce mortality, disrupt or impede growth, interfere with metamorphosis or other morphogenic functions, effect sterilization, or interfere with reproduction of the targeted termites. Suitable termiticides include but are not limited biological controls such as termite growth regulators, and materials that are toxic to termites (i.e., toxicants) such as chemical insecticides, pathogenic nematodes, fungi, protozoans, or bacteria. Preferred termiticides are slow-acting (i.e., acting over a course of hours, days, weeks, or preferably months), to reduce "avoidance" effects before individuals have distributed food to other members of the colony. A variety of slow-acting termiticides are known in the art, and include, for example silafluofen, borates (boric acid, disodium octaborate tetrahydrate), sulfluramid and other fluoroalkyl sulfonamides, avermectin, hydramethylnon, hexaflumuron and other chitin synthesis inhibitors and other acyl ureas, diflubenzuron (Dimilin), azadirachtin, dechlorane (Mirex), diiodomethyl-para-tolyl sulfone (A-9248), fluorosulfonates, imidacloprid, azadirachtin, cyromazine, juvenile hormones and juvenile hormone mimics or analogs such as fenoxycarb, methoprene, hydroprene, triprene, furnesinic acid ethyl and alkoxy derivatives, and pyriproxyfen (Nylar), and the plant *Rheuneo jupanic* Thunb. Roth. In addition, otherwise faster-acting insecticides may act more slowly and used by microencapsulation. Biological control agents that may be used as termiticides include fungi such as *Metarhizium anisopliae, Aspergillus flavus,* and *Beauveria bassiania,* nematodes such as *Neoplectana carpocapsae,* insect viruses, pathogenic bacteria such as *Bacillus thuringiensis* and *Serratia marcescens*, and toxins derived from biological control agents such as *B. thuringiensis* toxin.

The pesticidal compositions containing the nitrogen containing compounds of this invention may, for example, be formulated as wettable powders, dusts, granules, adherent dusts or granules, baits, solutions, emulsifiable concentrates, emulsions, suspension concentrates and aerosols. However, in a particularly preferred embodiment, the nitrogen containing compounds are formulated into a solid bait matrix as described above in combination with one of the above-mentioned termiticides. When the bait is placed in the vicinity of a termite colony, termites will preferentially feed on the treated bait, thereby consuming the toxicant, and thereafter introducing the termiticide to other members of the colony as well.

In an alternative embodiment, the nitrogen containing compounds may be used in combination with a colorant effective for perceptively marking a termite by contact therewith or by ingestion thereof. A variety of colorants are suitable for use herein, and include, but are not limited to inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum, and zinc. Use of neutral red is preferred.

Optionally, the nitrogen containing compounds may be further formulated with other insect attractants such as pheromones of the target termites or termite extracts containing pheromones. Termite pheromones suitable for use herein are generally well-known in the art, and include, for example, (Z,Z,E)-3,6,8-dodecatrien-1-ol, and the aggregation pheromone n-hexanoic acid. The composition may also include one or more additional termite attractants such as food odor attractants or aggregation attractants. Without being limited thereto, suitable food odor attractants are described by Peterson (U.S. Pat. No. 5,756,114), the contents of which are incorporated by reference herein.

The amount of the nitrogen containing compound is critical, and is selected to provide an effective feeding stimulus and aggregation of the target subterranean termite, and/or for masking the repellency to termites of other compounds. In a first embodiment, the effective amount is therefore defined herein as that quantity of nitrogen containing compounds that stimulate feeding and thus cause the target termites to aggregate to the location of a bait of the compounds at a rate significantly higher than the feeding stimulation and aggregation to a location without the compounds (i.e. negative control). Alternatively, in a second embodiment, an effective amount is defined as that quantity of nitrogen containing compounds that, when combined with otherwise termite repellent compounds such as described above, significantly reduces the number of termites repelled relative to the number of termites repelled by termite repellent compounds alone. In accordance with both embodiments of this invention, effective concentrations of the nitrogen containing compounds in the composition may vary between about 10 to 1,000 ppm (i.e., 0.001 to 0.1% by weight), preferably between about 100 to 500 ppm (0.001 to 0.05%, by weight), and most preferably about 450 ppm (0.045 %, by weight). The nitrogen containing compounds of this invention exhibit no significant toxicity to termites at the concentration levels less than or equal to about 1,000 ppm disclosed herein. Optimal amounts and concentrations may be readily determined by a practitioner skilled in the art, and will of course vary with the particular target termite, its population density, the size of the area to be treated, environmental conditions such as soil moisture, the occurrence of competing food sources, the type of vehicle or carrier, and particularly the cellulose source when used in a bait matrix. With respect to the latter, some woods normally contain amino acids, polypeptides and/or proteins which may be effective as termite aggregants and masking agents. For instance, aspen, spruce willow, pecan, ash, and red gum woods may contain amino acids at concentrations as high as approximately 290 ppm. Accordingly, with such woods, the amount of exogenous nitrogen containing compounds which must be added to the bait to raise the total concentration of nitrogen containing compounds (defined herein as the above described exogenous or added nitrogen containing compounds, plus endogenous amino acids, polypeptides or proteins within the wood) to an effective or preferred concentration as described above may therefore be lower. However, in any event, the amount of total nitrogen containing compounds in the composition or bait should not exceed approximately 1,000 ppm.

The aggregant compositions may be used in a number of ways, including monitoring or controlling termite populations. In one preferred embodiment, the aggregant composition is used for termite population monitoring capturing (hereinafter referred to as monitoring). The monitoring step of the process comprises monitoring particular location or locations to detect any termite activity, for example by capturing termites in a trap, examining bait matrices for evidence of consumption by termites, and/or capturing marked termites (i.e., which have consumed a colorant laced bait) at remote locations. Precise monitoring will enable identification of areas of need for control or termiticide application. In another preferred embodiment, the aggregants may be used to control pest populations by combination with an effective amount of an termiticide to kill the termites (as an attracticidal bait). Termiticide delivery is preferably effected by providing a bait matrix containing both the aggregant composition and termiticide as described hereinabove. In a particularly preferred embodiment both processes are conducted as sequential elements of an integrated termite management program, with an area of interest subjected to monitoring for termite activity, followed by termite control if activity is detected In the practice of any of the above-described embodiments, an aggregant is used as a bait or is otherwise applied to the locus of or in the vicinity of suspected infestation which is in an environment accessible to termites and subject to termite infestation and/or migration, and where a food source other than the aggregant composition or bait is accessible to the termites. In the preferred embodiment, the composition or bait is applied in the vicinity of a woody environments such as structures or buildings constructed at least in part from wood, lumber, dead or living trees, forests, orchards or other agricultural fields which are subject to termite attack. The aggregant containing composition or bait will be applied in an amount effective to stimulate feeding and aggregate the target termite, and/or mask the repellency of other compounds, as set forth hereinabove.

It is envisioned that the compounds may be used in conjunction with any type of appropriate bait or attractant disseminator as known in the art.

The following examples are intended only to further illustrate the invention and are not intended to limit the scope of the invention, which is defined by the claims.

EXAMPLE 1

The basic formulation of the matrix was prepared the same day that the experiment was set up, as reported by Rojas et al. (U.S. patent application Ser. Nos. 09/294,499 and 09/625,940, ibid). The colorant used was neutral red (Product number 72210, Fluka Chemical Corp., Milwaukee, Wis.) at 1000 ppm. In a choice test, this colorant has shown to be moderately deterrent to the Formosan termite.

Under a laminar flow hood, the sterile cellulose was weighed using a Oahus portable plus scale (Fisher Scientific, Pittsburgh, PA) into a sterile 600 ml glass beaker. The colorant was weighed using a Mettler Toledo balance (PB303, Fisher Scientific, Pittsburgh, Pa.) and added to the pre-weighed cellulose. The cellulose with the colorant were homogenized using a sterile stainless steel spatula.

The sterile liquid mixture was measured into a 50 ml sterile screw cap conical tube (Product number 62.547.004 PP, Sarstedt, Inc., Newton, N.C.) and the urea was added at each of the following doses: 0, 10, 20, 40, 80, 160, 320, 640, and 1280 ppm; then it was added to the colored cellulose to a 7:3 ratio, (liquid-urea:colored-cellulose) and mixed to homogenize. The control was bait matrix without colorant and without urea. Matrix presentation:

Five grams of bait matrix containing either a given dose of urea and colorant or control were packed into 50×9 mm sterile Petri dishes (Falcon 351006, Becton Dickinson, Franklin Lakes, N.J.). To allow the entrance of the termites to the dishes, a 2 mm in diameter hole on the side of the bottom part of each dish was made using a soldering iron.

Two hundred and fifty termite workers and 50 soldiers were previously placed into foraging arenas. Each foraging arena consisted of groups of 300 *C. formosanus* (250 workers and 50 soldiers) placed into two stacked Petri dishes connected by a central hole. The lower dish (150×25 mm) was filled with 200 ml of sand and top soil mix (1:1) (passed trough a No. 16 sieve), 100 ml of water and 1 g of polyacrylamide. The bottom of the top dish (150×15 mm) was glued to the cover of the lower dish and then connected vertically by melting through a 10 mm hole with a soldering iron. The lower dish functioned as a nesting site and the top dish as a foraging arena.

One treatment dish and one control dish were placed in the center of the top dish, taking care that the holes were facing each other and at least 1 cm apart. This experiment included 30 repetitions. Matrix consumption was checked 30 d after. The dishes were kept under dark in an environmental chamber (I-36VL, Percival Scientific, Boone, Iowa). Matrix consumption was measured 30 d after by removing the left over bait matrix from the dishes and weighed it using a Sartorius balance (BP 211D, VWR Scientific, Atlanta, Ga.).

The effect of the urea on reducing deterrence by the neutral red was measured by subtracting the consumed weight of colored matrix to the consumed weight of control matrix. This produces a consumption difference in favor of the control matrix. High numbers of this difference indicate higher levels of feeding deterrence. Mean consumption differences at different concentrations of urea were analyzed by Marquardt-Levenberg algorithm procedure of non-linear regression using Sigma plot 2000 Ver 6 for Windows (SPSS, Inc., Chicago, Ill.).

The results are shown in FIG. 1 as the difference of consumption (in grams) by groups of 300 Formosan subterranean termites between the blank bait matrix vs. bait matrices containing 1,000 ppm of the colorant neutral red, added as a feeding deterrent, and varying concentrations of urea. Formosan termites were expected to prefer the blank matrix over the colored matrix due to the repellency of the neutral red. However, the addition of urea to the colored matrix in different concentrations significantly affected the feeding deterrence induced by the colorant.

It is understood that the foregoing detailed description is given merely by way of illustration and that modifications and deviations may be made therein without departing from the spirit and scope of the invention.

We claim:

1. A composition for aggregating termites comprising a termiticidally effective amount of a termiticide and a nitrogen containing compound selected from the group consisting of ammonium salts and amine containing compounds exclusive of naturally occurring amino acids of proteins, polypeptides, or proteins, in an amount effective to stimulate termites to feed or mask the unattractiveness of other compounds in the composition or both, and wherein the concentration of said nitrogen containing compound in said composition is between about 10 to about 1000 ppm, and further wherein said nitrogen containing compound is not present in a termiticidally effective amount.

2. The composition of claim 1 further comprising water.

3. The composition of claim 2 further comprising a humectant.

4. The composition of claim 1 further comprising a bait matrix.

5. The composition of claim 4 wherein said bait matrix comprises a cellulose containing material.

6. The composition of claim 5 wherein said cellulose containing material comprises wood, and the total concentration of said nitrogen containing compound plus endogenous amino acids, polypeptides, and proteins in said wood, is between about 10 to about 1000 ppm.

7. The composition of claim 1 further comprising water, and a bait matrix.

8. The composition of claim 7 wherein said bait matrix comprises a cellulose containing material.

9. The composition of claim 8 wherein said cellulose containing material comprises wood, and the total concentration of said nitrogen containing compound plus endogenous amino acids, polypeptides, and proteins in said wood, is between about 10 to about 1000 ppm.

10. The composition of claim 7 further comprising a humectant.

11. The composition of claim 1 wherein said nitrogen containing compound is selected from the group consisting of urea, ureido compounds, uric acid, isomers of uric acid, derivatives of uric acid, amino benzoic acid, aminobenzoyl glutamic acid, amino butyric acid, aminonicotinic acid, aminophenol, aminosalicylic acid, aminonaphthols, aminonaphthoic acid, aminopurine, aminopyridine, benzylamines, aspartame, glucosamine, ammonium fluoride, and the ammonium salt of molibdic acid.

12. The composition of claim 11 wherein said nitrogen containing compound is selected from the group consisting of urea and uric acid.

13. A composition for aggregating termites comprising a bait matrix, a termiticide in a termiticidally effective amount, and a nitrogen containing compound selected from the group consisting of ammonium salts and amine containing compounds exclusive of naturally occurring amino acids of proteins, polypeptides, or proteins, in an amount effective to stimulate termites to feed or mask the unattractiveness of other compounds in the composition or both, and wherein the total concentration of said nitrogen containing compound in said composition plus any endogenous amino acids, polypeptides, and proteins in said bait matrix is between about 10 to about 1000 ppm, and further wherein said nitrogen containing compound is not present in a termiticidally effective amount.

14. The composition of claim 13 further comprising water.

15. The composition of claim 14 further comprising a humectant.

16. The composition of claim 13 wherein said bait matrix comprises a cellulose containing material.

17. The composition of claim 16 wherein said cellulose containing material comprises wood.

18. The composition of claim 14 wherein said bait matrix comprises a cellulose containing material.

19. The composition of claim 18 wherein said cellulose containing material comprises wood.

20. The composition of claim 18 further comprising a humectant.

21. The composition of claim 13 further comprising a colorant effective for marking subterranean termites.

22. The composition of claim 13 wherein said nitrogen containing compound is selected from the group consisting of urea, ureido compounds, uric acid, isomers of uric acid, derivatives of uric acid, amino benzoic acid, aminobenzoyl glutamic acid, amino butyric acid, aminonicotinic acid, aminophenol, aminosalicylic acid, aminonaphthols, aminonaphthoic acid, aminopurine, aminopyridine, benzylamines, aspartame, glucosamine, ammonium fluoride, and the ammonium salt of molibdic acid.

23. The composition of claim 22 wherein said nitrogen containing compound is selected from the group consisting of urea and uric acid.

24. The composition of claim 6 wherein the total concentration of said nitrogen containing compound plus any endogenous amino acids, polypeptides, and proteins in said wood is between about 100 to 500 ppm.

25. The composition of claim 13 wherein the total concentration of said nitrogen containing compound plus any endogenous amino acids, polypeptides, and proteins in said bait matrix is between about 100 to 500 ppm.

* * * * *